United States Patent [19]

Starks et al.

[11] 4,117,243

[45] Sep. 26, 1978

[54] PREPARATION OF O-BENZYLPHENOL

[75] Inventors: Charles M. Starks; Allan J. Lundeen, both of Ponca City, Okla.

[73] Assignee: Continental Oil Company, Ponca City, Okla.

[21] Appl. No.: 775,030

[22] Filed: Mar. 7, 1977

[51] Int. Cl.$^2$ ............................................. C07C 37/00
[52] U.S. Cl. ..................................................... 568/744
[58] Field of Search ................................... 260/619 R

[56] References Cited

U.S. PATENT DOCUMENTS 2,678,951  5/1954  Smith et al. ...................... 260/619 R
2,872,489  2/1959  Dietzler et al. .................. 260/619 R

OTHER PUBLICATIONS

McMaster et al., "Industrial and Engineering Chemistry", vol. 28 (1936), pp. 505–506.

*Primary Examiner*—Joseph E. Evans
*Attorney, Agent, or Firm*—Bayless E. Rutherford, Jr.

[57] ABSTRACT

A process for preparing o-benzylphenol is disclosed. The process comprises heating benzyl phenyl ether, either in liquid or vapor phase, in the presence of an effective amount of activated alumina catalyst.

5 Claims, No Drawings

PREPARATION OF O-BENZYLPHENOL

General Background o-Benzylphenol is useful as a dye leveling agent for polyester fibers. Usually, it is made by treatment of phenol with benzyl chloride or benzyl alcohol in the presence of a strong acid such as aluminum chloride, zinc chloride or sulfuric acid. Unfortunately, this method produces a substantial amount of p-benzylphenol. In addition, the method presents corrosion problems and difficult operating techniques.

It is thus apparent that it would be desirable to have a process which prepares o-benzylphenol in good selectivity (that is only a minor amount of para and meta isomers in the product). Our invention is directed to providing such a process.

Prior Art

A search of the prior art did not produce any reference teaching the specific process of our invention.

Brief Summary of the Invention

Briefly stated, the present invention is directed to a process for preparing o-benzylphenol by contacting benzyl phenyl ether, in liquid or vapor phase, at an elevated temperature with an effective amount of activated alumina catalyst.

In a preferred embodiment, the reaction admixture contains, additionally, phenol.

Detailed Description

A. Rearrangement of benzyl phenyl ether

Any activated alumina is suitable for use in our process.

A preferred activated alumina for use in our process is one prepared by the hydrolysis of aluminum alkoxides. The preferred activated alumina has the following properties:

| Crystal Structure | α-alumina monohydrate |
|---|---|
| Surface Area, meters/gram | 230 – 300 |
| $Al_2O_3$, weight percent* | 70 – 75 |
| Loose bulk density, grams/liter | 650 – 720 |

*substantially all of the remainder is water.

A particularly suitable activated alumina is available from Conoco Chemicals Division of Continental Oil Company under the trademark "CATAPAL" ®SB.

A suitable amount of catalyst is in the range of about 0.005 to about 1 part by weight per part of benzyl phenyl ether. On the same basis the preferred amount of catalyst is about 0.01 to about 0.1 part by weight.

Use of phenol in the reaction admixture is desirable in that it increases the selectivity to monobenzylphenols and decreases the amount of dibenzylphenols and higher boiling products. A suitable amount of phenol is in the range of about 0.1 to about 10 parts per part of benzyl phenyl ether. On the same basis, the preferred amount of phenol is in the range of about 1 to about 3 parts.

The process can be conducted either in liquid or vapor phase. When conducting the process in the liquid phase a suitable temperature is in the range of about 125 to about 450° C., with the preferred temperature being in the range of about 150° to about 350° C. When conducting the process in the vapor phase a suitable temperature is in the range of about 225° to about 450° C., with the preferred temperature being in the range of about 250° to about 350° C.

Conducting the process in liquid phase may require application of some pressure to keep the reactants in the liquid state. It should be noted that at some temperatures no pressure is required. In any case, the pressure in the process will be in the range of 0 to 70 atmospheres.

The reaction time for liquid phase operation is in the range of 0.1 to 8 hours. For vapor phase operation the reaction time is in the range of 0.1 to 60 minutes.

The fraction containing the desired o-benzylphenol product can be recovered from the organic product composition by means of fractional distillation.

B. Preparation of benzyl phenyl ether

A typical method of preparing benzyl phenyl ether is by the reaction of benzyl chloride and phenol in the presence of caustic (e.g. NaOH). Inasmuch as this method is well-known in the art a detailed discussion is not needed.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example shows the preparation of benzyl phenyl ether.

A mixture of 376 g (4.0 moles) of phenol and 160 g (4.0 moles) of sodium hydroxide were mixed and heated to reflux (154° C.). Water (10 ml) was added to help put all of the sodium hydroxide into solution. Benzyl chloride (506 g, 4.0 moles) was added dropwise over a period of about 1 hour, during which time the reflux temperature fell from 154° to 114°. Refluxing and stirring was continued for an additional hour, after which the reaction mixture was cooled to 90° and 500 ml water was added. The pH was adjusted to 1 by addition of concentrated HCl. The organic layer (upper phase) was separated, washed with 500 ml water (now the organic phase is the lower layer) and dried over 50 g of anhydrous sodium sulfate. Analysis of this product by GLC (15 feet × ⅛ inch SE 30, 100–350° at 10°/min.) showed the following:

| Component | Area % |
|---|---|
| Phenol | 10.17 |
| Benzyl chloride | 2.74 |
| Benzyl phenyl ether | 46.20 |
| o-Benzylphenol | 14.78 |
| p-Benzylphenol | 1.94 |
| o-Benzylphenyl benzyl ether | 6.82 |
| m,p-Benzylphenyl benzyl ether | 1.12 |
| 2,6-Dibenzyl phenol | 3.84 |
| 2,4/2,5-Dibenzyl phenol | 1.54 |
| Others | 12.39 |

EXAMPLE 2

This example shows the preparation of o-benzylphenol from the crude benzyl phenyl ether of Example 1 using our process (liquid phase conditions) wherein phenol is added to the reaction mixture. The process was as follows:

A mixture of 100 g crude benzyl phenyl ether, 100 g of phenol and 20 g of calcined CATAPAL ®SB alumina powder was heated under reflux (165–171° C. after 1.5 ml of water was taken over in the Dean-Stark trap) for 1.5 hours, after which a sample (A) was taken. After another hour of refluxing at 193–204° C. (some additional material taken over into the Dean-Stark trap) the reaction was stopped and a second sample (B) was taken. The samples were analyzed by GLC (15 feet × ⅛inch SE 30 column, 100–350° at 8°/min.). The results were as follows:

| Component | Area % Sample A | Area % Sample B |
|---|---|---|
| Phenol | 62.26 | 46.13 |
| Unknowns | 0.27 | 1.85 |
| Benzyl phenyl ether | 2.35 | 0.90 |
| o-Benzylphenol | 21.11 | 31.04 |
| m,p-Benzylphenol | 7.37 | 10.70 |
| Benzyl benzylphenyl ethers | 0.76 | 0.74 |
| 2,6-Dibenzylphenol | 3.48 | 4.79 |
| 2,4/2,5-Dibenzylphenols | 2.41 | 3.86 |

Of the total product mixture the selectivity of total benzylphenol was 81.6%, of which 74.4% was o-benzylphenol and 25.6% m,p-benzylphenol.

EXAMPLE 3

This example shows the preparation of o-benzylphenol from the crude benzyl phenyl ether of Example 1 using our process (liquid phase conditions) wherein no phenol is added to the reaction mixture. The process was as follows:

Crude benzyl phenyl ether (100 g) was heated to 140–170° over a period of 4 hours with 5.0 g of calcined CATAPAL®SB powder. Samples of the product were analyzed after 2 hours, and again after 4 hours of reaction time as follows:

| | Area % in Feed | Area % in 2 Hr. Sample | 4 Hr. Sample |
|---|---|---|---|
| Phenol | 10.2 | 14.2 | 19.0 |
| Benzyl chloride | 2.7 | 2.1 | 0.7 |
| Benzyl phenyl ether | 46.2 | 32.2 | 0.4 |
| o-Benzyl phenol | 14.8 | 20.8 | 37.5 |
| m,p-Benzyl phenol | 1.9 | 4.3 | 10.8 |
| Benzyl benzylphenyl ethers | 7.9 | 15.5 | 3.0 |
| 2,6-Dibenzyl phenol | 3.8 | 4.3 | 14.8 |
| 2,4/2,5-Dibenzyl phenol | 1.5 | 4.6 | 13.1 |
| Others | 12.4 | 2.0 | 0.7 |

The low concentration of phenol in this reaction composition results in a 60.5% selectivity of product mixture containing 77.6% o-benzylphenol and 22.4% m,p-benzylphenol.

EXAMPLE 4

This example shows the preparation of o-benzylphenol from crude benzyl phenyl ether which was prepared as in Example 1 and therefore contained some o-benzylphenol and m,p-benzylphenol. The crude benzyl phenyl ether was vaporized and passed over CATAPAL®SB alumina (1/16 inch extrudate) at 325° C. with a liquid hourly space velocity of 2.2 (volume). GLC analyses of the feed and product are shown below.

| | Area % in Feed | Area % in Product |
|---|---|---|
| Phenol | 5.3 | 25.0 |
| Benzyl phenyl ether | 80.4 | 0.4 |
| o-Benzylphenol | 10.4 | 46.2 |
| m,p-Benzylphenol | 1.0 | 0.3 |
| Dibenzylphenols | — | 22.6 |
| Unknowns | 2.9 | 5.4 |

From the results the selectivity to o-benzylphenol was 62%.

EXAMPLE 5

This example shows the preparation of benzyl phenyl ether and the conversion of benzyl phenyl ether to o-benzylphenol (liquid phase process).

The example also provides a material balance for the entire process.

A mixture of 132 g (3.30 moles) of sodium hydroxide, 564 g (6.0 moles) of phenol and 132 g of water was charged to a 3-necked flask fitted with a mechanical stirrer, thermometer, addition funnel, reflux condenser and Dean-Stark trap. The reaction mixture was heated to reflux (130°) and addition of benzyl chloride was started. After 1 hour all (380 g, 3.0 moles) of the benzyl chloride had been added and the reflux temperature had dropped to 108° C. Toluene (25 ml, 21 g) was added to help take off water, and heating and stirring were continued with water being removed. After essentially all the water had been removed (231 g, 2 more hours, final reflux temperature = 191°) the reaction mixture was cooled and a sample (1) was taken.

To the crude reaction mixture above, CATAPAL®SB alumina (10 g) was added and refluxing was conducted for 3 hours with hourly sampling. Analysis of these samples (Samples 2 and 3) showed that little, if any, rearrangement of the benzyl phenyl ether occurred.*

* Apparently, this was due to the presence of sodium salts in the ether product which deactivated the catalyst.

The reaction mixture was mixed with 992 g of water, filtered, and the water phase was separated (922 g of of water phase recovered). The organic phase was washed with 993 g of water (1013 g of water phase recovered). The organic phase, along with 25 ml of toluene, was added back to the reaction flask, and heated under reflux to take off water in the Dean-Stark trap (ca 7 ml H₂O). CATAPAL®SB alumina (10 g) was added and the reaction mixture and refluxing was continued for 5 hours with hourly sampling (Samples 4 to 8). Analysis of these samples indicated very slow conversion to rearrangement products. Then, 40 g of calcined CATAPAL®SB powder was added and refluxing was continued for 2 hours. At this point analysis of the reaction mixture (Sample 9) indicated substantially complete rearrangement of benzyl phenyl ether. The results of the analyses are shown in the following table.

| | Analysis of Samples*,** Area % for Sample No. | | | | | | | | |
|---|---|---|---|---|---|---|---|---|---|
| Component | 1 | 2 | 3 | 4 | 5 | 6 | 7 | 8 | 9 |
| Phenol | 35.3 | 34.8 | 39.2 | 33.5 | 36.9 | 35.1 | 32.3 | 30.8 | 33.8 |
| Benzyl phenyl ether | 45.9 | 44.1 | 43.9 | 46.7 | 44.3 | 45.1 | 45.7 | 43.6 | 0.4 |
| o-Benzylphenol | 12.2 | 11.6 | 11.4 | 12.8 | 12.3 | 13.1 | 14.2 | 17.5 | 54.5 |
| m,p-Benzylphenol | 2.3 | 1.7 | 1.6 | 2.4 | 2.2 | 2.3 | 2.4 | 2.5 | 2.2 |

-continued

| | Analysis of Samples*,** | | | | | | | | |
|---|---|---|---|---|---|---|---|---|---|
| | Area % for Sample No. | | | | | | | | |
| Component | 1 | 2 | 3 | 4 | 5 | 6 | 7 | 8 | 9 |
| Benzyl o-Benzyl phenyl ether | 1.9 | 1.8 | 1.7 | 2.0 | 1.9 | 1.9 | 2.0 | 2.2 | 1.5 |
| Benzyl m,p-Benzyl phenyl ether | 0.7 | 0.6 | 0.6 | 0.8 | 0.7 | 0.7 | 1.0 | 1.2 | — |
| 2,6-Dibenzylphenol | 1.5 | 1.4 | 1.3 | 1.5 | 1.3 | 1.4 | 1.7 | 1.5 | 5.1 |
| 2,4/2,5-Dibenzylphenol | 0.3 | 0.3 | 0.3 | 0.4 | 0.4 | 0.5 | 0.6 | 0.8 | 2.6 |

*on a toluene free basis
**using a 15' × 1/8" SE 30 column, 100–350° C at 8°/min.

The final product was filtered away from the catalyst using vacuum, and charged directly to a distillation flask. The actual weight of charge was 609.7 g, as compared to 859 g theoretical. The loss of 250 g was due to phenol loss in the Dean-Stark trap ($\approx$25 g), adsorption of material into the alumina ($\approx$30–40 g), samples (9 g), phenol in water (40 g) and unaccounted losses (136 g). The product was distilled on a 4 foot × 1 inch column. The results were as follows:

| Cut. No. | b.p. (20 Torr) | Wt. (g) | Wt. % of Charge |
|---|---|---|---|
| 1 | 34 – 162 | 172.1 | 28.2 |
| 2 | 162 – 188 | 334.3 | 54.8 |
| 3 | 188 (20 Torr) – 245 (1 Torr) | 67.9 | 11.1 |
| Trap | | 13.2 | 2.2 |
| Residue | | 19.7 | 3.2 |
| L&H | | 2.5 | 0.4 |

The composition of the distillation cuts was as follows:

| | Feed | | Cut 1 | | Cut 2 | | Cut 3 | |
|---|---|---|---|---|---|---|---|---|
| | Wt. % | Wt. (g) | Area% | Wt. (g) | Area% | Wt. (g) | Area% | Wt. (g) |
| Toluene | 3.6 | 22.0 | 0.6 | 1.1 | tr | — | 0.9 | 0.6 |
| Phenol | 32.3 | 196.9 | 97.9 | 168.4 | tr | — | — | — |
| Benzyl phenyl ether | 0.4 | 2.1 | 0.3 | 0.6 | tr | — | — | — |
| o-Benzylphenol | 52.0 | 317.3 | 0.4 | 0.7 | 93.4 | 312.1 | 12.4 | 8.4 |
| m,p-Benzylphenol | 2.1 | 12.6 | 0.3 | 0.6 | 1.9 | 6.2 | 9.4 | 6.4 |
| Benzyl benzyl phenyl ethers | 1.5 | 9.0 | — | — | 2.7 | 8.9 | 7.2 | 4.9 |
| 2,6-Dibenzylphenol | 4.9 | 29.6 | — | — | 0.9 | 3.2 | 47.5 | 32.3 |
| 2,4/2,5-Dibenzylphenol | 2.5 | 15.2 | — | — | 1.1 | 3.8 | 22.3 | 15.2 |

In summary, this example shows the following. If one assumes that by avoiding the losses noted above, and using the product distributions above, then one could obtain a product containing approximately 85% o-benzylphenol and 15% p-benzylphenol in an overall selectivity of about 73%, based on using benzyl chloride as starting material.

Thus, having described the invention in detail, it will be understood by those skilled in the art that certain variations and modifications may be made without departing from the spirit and scope of the invention as defined herein and in the appended claims.

We claim:

1. A process for preparing o-benzylphenol wherein the process comprises contacting benzyl phenyl ether in the presence of an effective amount of activated alumina in the liquid phase at a temperature in the range of about 125° to about 450° C. and a pressure of 0 to 40 atmospheres.

2. The process of claim 1 wherein the amount of activated alumina is in the range of about 0.005 part to about 1 part by weight based on the benzyl phenyl ether.

3. The process of claim 2 wherein the reaction admixture contains additionally about 0.1 to 10 parts of phenol per part of benzyl phenyl ether.

4. The process of claim 3 wherein:
   (a) the amount of activated alumina is in the range of about 0.01 to about 0.1 part by weight, and
   (b) the temperature is in the range of about 150° to about 350° C.

5. The process of claim 4 wherein the activated alumina has the following properties:

| Crystal Structure | α-alumina monohydrate |
|---|---|
| Surface Area, meters/gram | 230 – 300 |
| Al$_2$O$_3$, weight percent | 70 – 75 |
| Loose bulk density, grams/liter | 650 – 720 |

* * * * *